United States Patent [19]
Cooper et al.

[11] Patent Number: 5,919,756
[45] Date of Patent: Jul. 6, 1999

[54] AMIDES

[75] Inventors: Robin David Grey Cooper; Michael John Rodriguez, both of Indianapolis; Nancy June Snyder, Charlottesville; Mark James Zweifel, Indianapolis, all of Ind.

[73] Assignee: Eli Lilly and Company, Indianapolis, Ind.

[21] Appl. No.: 08/847,069

[22] Filed: May 1, 1997

Related U.S. Application Data

[60] Provisional application No. 60/020,774, Jun. 28, 1996.

[51] Int. Cl.$^6$ .......................... A61K 38/12; A61K 38/08; C07K 7/00; C07K 9/00
[52] U.S. Cl. ...................... 514/8; 514/9; 514/11; 514/450; 530/317; 530/322; 530/323; 530/329; 540/459
[58] Field of Search ................................. 530/317, 322, 530/323, 329; 514/9, 11, 8, 450; 540/459

[56] References Cited

U.S. PATENT DOCUMENTS

| | | | |
|---|---|---|---|
| 4,845,194 | 7/1989 | Glass et al. | 530/344 |
| 5,071,749 | 12/1991 | Kondo et al. | 530/317 |
| 5,194,424 | 3/1993 | Malabarba et al. | 514/8 |
| 5,312,738 | 5/1994 | Hamill et al. | 435/75 |
| 5,534,420 | 7/1996 | Debono et al. | 435/71.3 |
| 5,591,714 | 1/1997 | Nagarajan et al. | 514/9 |

FOREIGN PATENT DOCUMENTS

| | | |
|---|---|---|
| 365319 | 4/1990 | European Pat. Off. . |
| 0 435 503 | 7/1991 | European Pat. Off. . |
| 0 667 353 | 8/1995 | European Pat. Off. . |
| 667353 | 8/1995 | European Pat. Off. . |

WO 9630401 10/1996 WIPO .

OTHER PUBLICATIONS

Goldstein et al. Lett. Pept. Sci. (1995), 2(¾), 125–34, 1995.
Sundram, et al., *J. Org. Chem.*, 60, 1102–1103 (1995).
Derwent Abstract 86–101547/16, Oct. 11, 1984–GB–025685 (Apr. 16, 1986).
Malabarba, et al., *J. Antibiotics*, vol. 48, No. 8, 869–883 (1995).
Malabarba, et al., *J. Antibiotics*, vol. 46, No. 4, 668–675 (1993).
Malabarba, et al., *J. Med. Chem.*, vol. 35, No. 22, 4054–4060 (1992).
Shi, et al., *J. Am. Chem. Soc.*, vol. 115, No. 15, 6482–6486 (1993).
Malabarba, et al., *J. Med. Chem.*, vol. 32, No. 11, 2450–2460 (1989).
Pavlov, et al., *J. Antibiotics*, vol 49, No. 2, 194–198 (1996).
Malabarba, et al., *Abstracts of the 33$^{rd}$ ICAAC*, "A New Semisynthetic Glycopeptide Antibiotic Active Against Highly Glycopeptide–Resistant Enterococci", Abstract 445, p. 200.
T.I. Nicas, et al., *Antimicrobial Agents and Chemotherapy*, 1477–1481 (Sept., 1989).
R. Nagarajan, et al., *J. Antibiotics*, vol. XLII, No. 1, 63–72 (1996).

*Primary Examiner*—Mukund J. Shah
*Assistant Examiner*—Bruck Kifle
*Attorney, Agent, or Firm*—Arlene K. Musser

[57] ABSTRACT

The present invention is directed to amides of antibiotic A82846B (also known as chloroorienticin A), and of $N^4$-derivatives of A82846B. The present amide compounds are useful as antibacterials, especially for the control of gram positive bacteria; the compounds are particularly useful for the control of resistant bacterial strains, such as vancomycin-resistant-enterococci ("VRE").

14 Claims, No Drawings

AMIDES

CROSS-REFERENCE TO RELATED APPLICATION

This is a continuation-in-part of copending application Ser. No. 60/020,774, filed Jun. 28, 1996.

BRIEF SUMMARY OF THE INVENTION

The present invention is directed to glycopeptide amides, more particularly to amides of antibiotic A82846B, also known as chloroorienticin A, and of $N^4$-derivatives of A82846B. These amides are useful as antibacterials, especially for the control of gram positive bacteria; the compounds are particularly useful for the control of resistant bacterial strains, such as vancomycin-resistant-enterococci ("VRE").

DETAILED DESCRIPTION OF THE INVENTION

The compounds of the present invention are defined by Formula I:

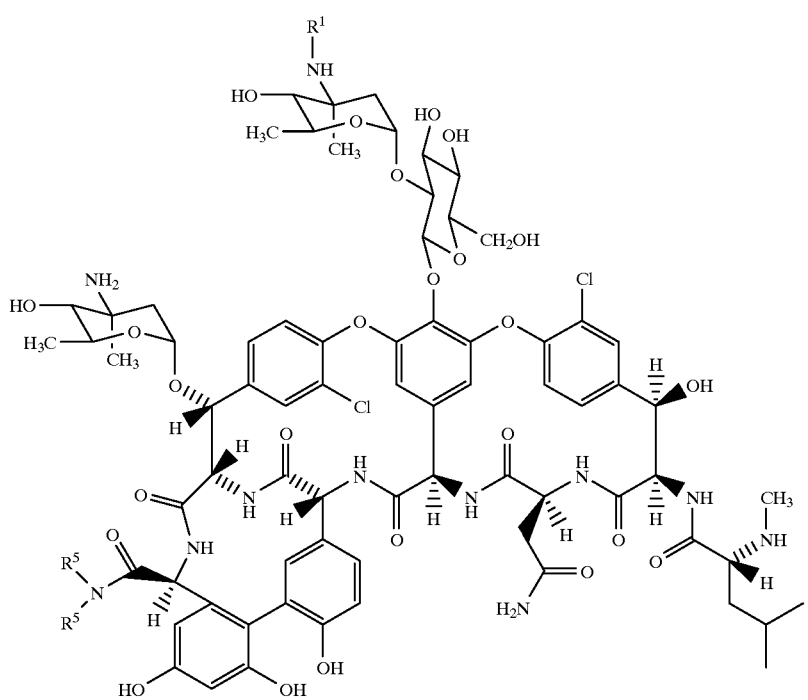

wherein $R^1$ is:
  hydrogen or $-CH_2R^2$;
wherein $R^2$ is:
  hydrogen,
  alkyl of $C_1$–$C_{15}$,
  alkenyl of $C_2$–$C_{15}$,
  alkynyl of $C_2$–$C_{15}$,
  haloalkyl of $C_1$–$C_7$,
  acenaphthenyl,
  2-fluorenyl,
  9,10-dihydro-2-phenanthrenyl,
  $R^3$,
  alkyl of $C_1$–$C_{11}$—$R^3$,
  alkenyl of $C_2$–$C_7$—$R^3$,
  alkynyl of $C_2$–$C_7$—$R^3$, or
  alkyl of $C_1$–$C_7$—O—$R^3$,
wherein $R^3$ is a radical of the formula:

$$-R_4-[\text{linker}_{(0 \text{ or } 1)}-R^4]_{(0 \text{ or } 1)}$$

wherein each $R^4$ independently represents phenyl, cycloalkyl of $C_5$–$C_6$, naphthyl, or thienyl, each of which is unsubstituted or is optionally substituted with one or two substituents, each of which is independently alkyl of $C_1$–$C_{10}$, haloalkyl of $C_1$–$C_2$, haloalkoxy of $C_1$–$C_2$, alkoxy of $C_1$–$C_{10}$, halo, cyano, or nitro;
and "linker" is:
  -alkylene of $C_1$–$C_3$,
  —O—alkylene of $C_1$–$C_6$,
  -alkylene of $C_1$–$C_6$—O—,
  —O—, —N(H or loweralkyl of $C_1$–$C_3$)—,
  —S—,
  —SO—,
  —SO$_2$—, $-NH-\underset{\underset{O}{\|}}{C}-$,  $-\underset{\underset{O}{\|}}{C}-NH-$,  $-CH=CH-$, $-C\equiv C-$,  $-N=N-$,  $-O-\underset{\underset{O}{\|}}{C}-$, or $-\underset{\underset{O}{\|}}{C}-O-$;

and wherein $R^5$ is defined as follows:
(1) each $R^5$ independently represents
  hydrogen,
  cycloalkyl of $C_5$–$C_6$,
  cycloalkenyl of $C_5$–$C_6$,
  phenyl or substituted phenyl bearing from one to three
    substituents, each of which is independently
    halo,
    nitro,
    loweralkyl of $C_1$–$C_4$,
    cycloalkyl of $C_5$–$C_6$,
    loweralkoxy of $C_1$–$C_4$,
    haloloweralkyl of $C_1$–$C_4$, or
    haloloweralkoxy of $C_1$–$C_4$;
  naphthyl,
  biphenylyl,
  radical of the formula —$R^6$—$(R^7)_{0, 1, or 2}$, wherein $R^6$ is
    loweralkyl of $C_1$–$C_8$ optionally substituted by from one
    to three substituents, each of which is independently
    selected from the group consisting of halo, nitro, cyano,
    loweralkoxy of $C_1$–$C_4$, haloloweralkyl of $C_1$–$C_4$, and
    haloloweralkoxy of $C_1$–$C_4$; and $R^7$ is

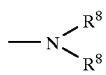

wherein each $R^8$ is independently hydrogen or loweralkyl of $C_1$–$C_4$ or one $R^8$ is hydrogen and the other $R^8$ is tert-butoxycarbonyl, or $R^7$ is phenyl or substituted phenyl as defined above, or (2) one $R^5$ is hydrogen and the other $R^5$ is (2-furanon-3-yl); or (3) both $R^5$s are taken together with the nitrogen and constitute a five- to seven-membered heterocyclic ring optionally containing in addition to the indicated nitrogen atom one additional hetero ring atom which is nitrogen, oxygen, or sulfur, and which heterocyclic radical can be unsubstituted or substituted with from one or two substituents, each of which is loweralkyl of $C_1$–$C_2$, loweralkoxy of $C_1$–$C_2$, phenyl, benzyl, or $C_1$–$C_6$-alkanoyl; or a salt thereof.

Certain compounds of the present invention are preferred. Amides of A82846B derivatives ($R^1$=—$CH_2R^2$) generally exhibit antibacterial activity at concentrations lower than the amides of A82846B itself ($R^1$=H). Antibacterial activity is further enhanced by employing certain "—$CH_2R^2$" groups such as the following:

(4-phenylbenzyl)
(4-(4-chlorophenyl)benzyl)
(4-(4-methylphenyl)benzyl)
(4-phenoxybenzyl)
((4-n-butylphenyl)benzyl)
(4-benzylbenzyl)

Primary amines ($H_2N$—$R_5$) may sometimes be preferred, for availability of starting materials and convenience of synthesis. Compounds wherein $R^2$=$R^3$ are also preferred. Other preferences will be apparent from the further teachings herein.

The compounds of the present invention are prepared by reacting A82846B ($R^1$=hydrogen) or an $N^4$-derivative thereof ($R^1$=—$CH_2R^2$), defined by Formula II:

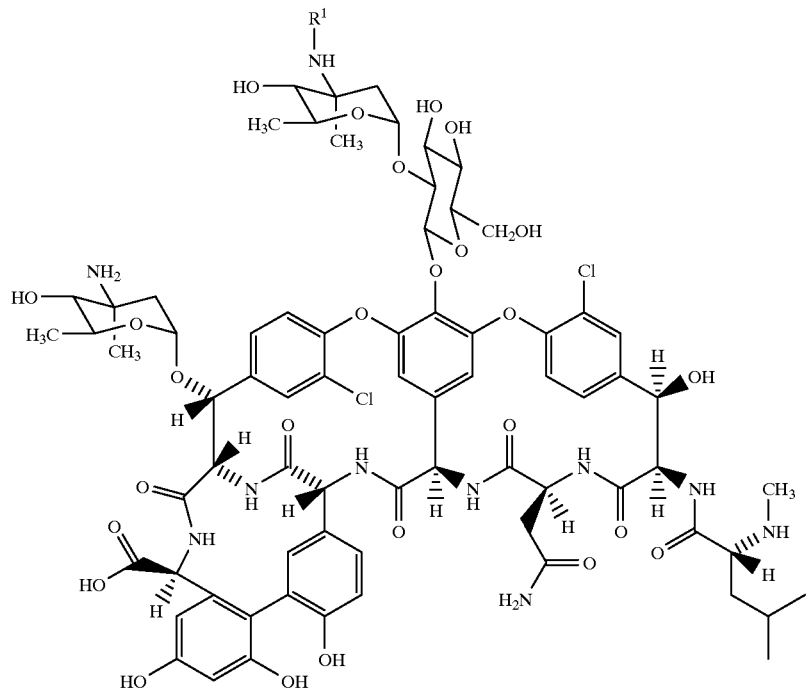

II with an amine of the formula

The Formula II compounds are known or prepared in standard procedures. A82846B ($R^1$=hydrogen) is the subject of U.S. Pat. No. 5,312,738. The derivatives, those compounds of Formula II wherein $R^1$ is —$CH_2R^2$, are prepared from A82846B by reductive alkylation. A82846B is initially reacted with an aldehyde to form an intermediate Schiff's base, which is subsequently reduced to obtain the desired Formula II compound. Alkylation at the $N^4$ position, in preference to other reactive sites in the molecule, is favored by supplying a source of soluble copper. Copper (II) acetate is a preferred source of copper. The copper is preferably supplied in an amount equimolar with the A82846B. Examples of the Formula II compounds are to be found in EPO 667,353, published Aug. 16, 1995.

The reaction of Formula II compounds and amines of the formula

yields the compounds of the present invention. The reaction conditions are not critical. The reaction proceeds well when carried out in a solvent such as DMF, DMSO, or a mixture of DMF and DMSO, and at reaction temperatures of 0 to 100° C., although the reaction is conveniently conducted at room temperature. Generally, the reaction is conducted with equimolar proportions of the reactants or an excess of the amine.

The reaction is facilitated by the use of a coupling agent, such as:

a) benzotriazol-1-yloxy-tripyrrolidinophosphonium hexafluorophosphate, one form of which is sold under the trademark PyBOP® (Calbiochem-Novabiochem AG);

b) benzotriazol-1-yloxytris(dimethylamino)phosphonium hexafluorophosphate ("BOP");

c) 0-benzotriazol-1-yl-N,N,N'N'-tetramethyluronium hexafluorophosphate ("HBTU");

d) 1,3-dicyclohexylcarbodiimide ("DCC"), alone or in combination with 1-hydroxybenzotriazole hydrate ("HOBT");

e) N,N'-dicyclohexyl-4-morpholinecarboxamidine ("WSC"); and f) (2-ethoxy-1-ethoxycarbonyl)-1,2-dihydroquinoline ("EEDQ").

The first listed of these is preferred. In general, the coupling agent is supplied in an equimolar amount or in an excess.

The product can be isolated by precipitation or by lyophilization of the reaction mixture, and purified if desired in a conventional manner, such as by HPLC. Characterization of products is best accomplished by Fast Atom Bombardment Mass Spectroscopy (FAB·MS).

When it is desired to employ a salt, a compound of the present invention can be reacted with a mineral or organic acid, in techniques well known to those skilled in the art. Pharmaceutically-acceptable salts are preferred.

The following example reports the preparation of an exemplary compound of the present invention.

EXAMPLE 1

$N^4$-(4-PHENOXYBENZYL)A82846B, 3-(DIMETHYLAMINO)PROPYLAMIDE, TRIFLUOROACETATE SALT

A mixture of $N^4$-(4-phenoxybenzyl)A82846B, trifluoroacetate salt, (0.668 g, 0.376 mmol, 1.0 equivalent) in 25 ml dimethylsulfoxide (DMSO) under an atmosphere of argon was treated with 3-(dimethylamino)propylamine (0.038 g, 0.376 mmol, 1.0 eq.) and benzotriazol-1-yloxy-tripyrrolidinophosphonium hexafluorophosphate (PyBOP®) (0.196 g, 0.376 mmol, 1.0 eq). The mixture was stirred at room temperature for 1 hour, diluted with 100 ml $H_2O$, and lyophilized to give a solid.

The analytical method for analysis was 15% $CH_3CN$/ 0.1% TFA at time 0 to 80% $CH_3CN$/0.1% TFA at 15 minutes. The UV wavelength used was 235 nm and the flow rate 2 ml/minute. Analysis was done using a Waters Nova-pak C18 RCM column (8×100 mm) with a Nova-pak C18 guard insert. The solid was purified by preparative reverse-phase high performance liquid chromatography (HPLC) using a Waters 3×(40×100 mm) C18 Nova-pak cartridge with Waters C18 Nova-pak guard insert and utilizing a TFA buffer system. The desired fraction was lyophilized to give the trifluoroacetate salt, a white solid (0.455 g, 55%). The product was characterized by FAB·MS, (M+3H), 1860.

Other products of the present invention were prepared as in Example 1 or with some modifications of the procedure. Modifications included varying the solvent, providing a longer reaction time, up to 123 hours, increasing the amount of amine and/or coupling agent up to 5 equivalents, and using the compound of Formula I as a free base. The reaction appeared to work best with DMSO, but DMF was easier to remove. The reaction was analyzed by HPLC to determine if product was present; if the reaction was incomplete, more amine (1–5 eq) and coupling agent (1–5 eq) were added with solvent and the reaction was continued from 3.5 hours to 48 hours longer.

Other examples of the present invention are listed in Table 1.

TABLE I

| Ex. No. | $R^5$ | $R^1$ | Name | Yield | Mass Spec. FAB-MS (M + 3H) |
|---|---|---|---|---|---|
| 2 | $CH_3$— | 4-phenylbenzyl | $N^4$-(4-phenylbenzyl)A82846B, methylamide, trifluoroacetate salt | 52 | 1773 |
| 3 | n-$C_4H_9$— | 4-phenylbenzyl | $N^4$-(4-phenylbenzyl)A82846B, n- | 19 | 1814 |

TABLE I-continued

| Ex. No. | R⁵ | R¹ | Name | Yield | Mass Spec. FAB-MS (M + 3H) |
|---|---|---|---|---|---|
|  |  |  | butylamide, trifluoroacetate salt |  |  |
| 4 | (CH₃)₃—C— | 4-phenylbenzyl | N⁴-(4-phenylbenzyl)A82846B, tert-butylamide, trifluoroacetate salt | 38 | 1814 |
| 5 | (CH₃)₃—C— | 4-phenoxybenzyl | N⁴-(4-phenoxybenzyl)A82846B, tert-butylamide, trifluoroacetate salt | 8.5 | 1831 |
| 6 | n-C₈H₁₇— | 4-phenoxybenzyl | N⁴-(4-phenoxybenzyl)A82846B, n-octylamide, trifluoroacetate salt | 27 | 1885 |
| 7 | 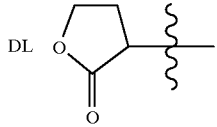 | 4-phenylbenzyl | N⁴-(4-phenylbenzyl)A82846B, DL-(2-furanon-3-yl)amide | 20 | 1841 |
| 8 | 4-cyclohexylphenyl | 4-phenylbenzyl | N⁴-(4-phenylbenzyl)A82846B, (4-cyclohexylphenyl) amide, trifluoroacetate salt | 8 | 1915 |
| 9 | benzyl | 4-phenoxybenzyl | N⁴-(4-phenoxybenzyl)A82846B, benzylamide, trifluoroacetate salt | 30 | 1864 |
| 10 | benzyl | 4-phenylbenzyl | N⁴-(4-phenylbenzyl)A82846B, benzylamide | 47 | 1849 |
| 11 | benzyl | 4-phenylbenzyl | N⁴-(4-phenylbenzyl)A82846B, benzylamide, HCl salt |  |  |
| 12 | 4-methoxybenzyl | 4-phenylbenzyl | N⁴-(4-phenylbenzyl)A82846B, (4-methoxybenzyl) amide, trifluoroacetate salt | 43 | 1878 |
| 13 | 3-methoxypropyl | 4-phenylbenzyl | N⁴-(4-phenylbenzyl)A82846B, (3-methoxypropyl)amide | N.D. | 1830 |
| 14 | phenethyl | 4-phenoxybenzyl | N⁴-(4-phenoxybenzyl)A82846B, phenethylamide, trifluoroacetate salt | 27 | 1880 |
| 15 | phenethyl | (4-n-butylbenzyl) | N⁴-(4-n-butylbenzyl)A82846B, phenethylamide, trifluoroacetate salt | N.D. | 1842 |
| 16 | phenethyl | hydrogen | A82846B, phenethylamide, trifluoroacetate salt | 27 | 1696 |
| 17 | phenethyl | 4-phenylbenzyl | N⁴-(4-phenylbenzyl)A82846B, phenethylamide | 58 | 1862 |
| 18 | phenethyl | 4-phenylbenzyl | N⁴-(4-phenylbenzyl)A82846B, phenethylamide, HCl salt | 37 | 1862 |
| 19 | phenethyl | 4-(4-methylphenyl)-benzyl | N⁴-(4-(4-methylphenyl)benzyl)-A82846B, phenethylamide | 15 | 1875 |
| 20 | 3-phenyl-n-propyl | hydrogen | A82846B, (3-phenyl-n-propyl) amide | N.D. | 1710 |
| 21 | (CH₃)₂N—CH₂—CH₂—CH₂— | 4-phenylbenzyl | N⁴-(4-phenylbenzyl)A82846B, (3-(dimethylamino)-n-propyl) amide | 26 | 1844 |
| 22 | 3,3-diphenyl-n-propyl | 4-phenylbenzyl | N⁴-(4-phenylbenzyl)A82846B, (3,3-diphenyl-n-propyl) amide | 16 | 1953 |
| 23 | (CH₃)₂N—CH₂—CH₂—CH₂— | hydrogen | A82846B, (3-(dimethylamino)-n-propyl)amide, trifluoroacetate salt | 19 | 1678 |
| 24 | benzyl | hydrogen | A82846B, benzylamide, trifluoroacetate salt | 48 | 1682 |
| 25 | 5-(tert-butoxycarbonylamino)-pentyl | 4-(4-chlorophenyl)-benzyl | N⁴-(4-(4-chlorophenyl)benzyl)-A82846B, 5-(tert-butoxycarbonylamino)-pentylamide, tris(trifluoroacetate) salt | 21 | 1976 |
| 26 | 5-aminopentyl | 4-(4-chlorophenyl)-benzyl | N⁴-(4-(4-chlorophenyl)benzyl)A82846B, 5-aminopentylamide, tetra(trifluoroacetate) salt | 61 | 1878 |

The invention is further illustrated by Examples 25 and 26.

EXAMPLE 25

N⁴-(4-(4-CHLOROPHENYL)BENZYL)A82846B, 5-(TERT-BUTOXYCARBONYLAMINO) PENTYLAMIDE, TRIS(TRIFLUOROACETATE) SALT

A mixture of N⁴-(4-(4-chlorophenyl)benzyl)A82846B, diphosphate salt (0.5 g, 0.251 mmol, 1.0 equivalent) in 8 ml dimethylformamide (DMF) and 4 ml dimethylsulfoxide (DMSO) under an atmosphere of nitrogen was treated with benzotriazol-1-yloxytripyrrolidinophosphonium hexafluorophosphate (PyBop®) (0.261 g, 0.502 mmol, 2.0 eq), N,N-diisopropylethylamine (0.097 g, 131 μl, 0.75 mmol, 3.0 eq), and N-(tert-butoxycarbonylamino)-1,5-diaminopentane (105 μl, 0.50 mmol, 2 eq). The mixture was stirred at room temperature for 5 days, then diluted with 80 ml acetone to produce a precipitate. The solid was collected by filtration to yield 526 mg of crude solid.

The analytical method for analysis was 100/0–25/75%, A/B over 30 minutes (A-0.1% TFA, 5% acetonitrile in water and B-acetonitrile). The UV wavelength used was 235 nm and the flow rate was 2 ml/minute. Analysis was done using a Waters μ bondapak™ C18 column (3.9×300 mm, 10 μm, 125 A).

The solid was purified by preparative reverse-phase high performance liquid chromatography (HPLC) on a Waters Prep 2000 system using a Waters Nova-pak® C18 cartridge [3×(40×100 mm), 6 μm, 60 A] with a Waters Nova-pak® C18 guard insert. The solvent system utilized was 0/100–75/25, B/C over 30 minutes (B-acetonitrile and C=0.1% TFA, 5% acetonitrile in water). The UV wavelength used was 235 nm and the flow rate was 50 ml/minute. The titled product was isolated (125 mg, 21% yield) and characterized by FAB-MS: calcd for $C_{96}H_{117}Cl_3N_{12}O_{27}$ 1974.7, found 1976.2 (M+2H).

EXAMPLE 26

N⁴-(4-(4-CHLOROPHENYL)BENZYL)A82846B, 5-AMINOPENTYLAMIDE, TETRA (TRIFLUOROACETATE) SALT

A mixture/suspension of N⁴-(4-(4-chlorophenyl)benzyl)-A82846B, 5-(tert-butoxycarbonylamino)pentylamide, tris (trifluoroacetate) salt, 0.125 g, 0.0539 mmol, 1 eq) in 15 ml dichloromethane was treated with trifluoroacetic acid (500 μl, 6.49 mmol, 120.4 eq) at 0° C. The reaction was stirred and allowed to warm to room temperature over 2.25 hours. A residue adhered to the side of the flask and was dissolved by adding methanol. The solvents were removed under vacuum and the residue was azeotroped with toluene (2X) to yield a white solid. The solid was analyzed and purified as above to yield the titled product (77 mg, 61% yield). The material was characterized by FAB-MS: calcd for $C_{91}H_{109}Cl_3N_{12}O_{25}$ 1874.7, found 1877.7 (M+3).

The compounds of Formula I are useful for the treatment of bacterial infections. Therefore, in another embodiment, the present invention is directed to a method for controlling a bacterial infection in a host animal, typically a warm-blooded animal, which comprises administering to the host animal an effective, antibacterial amount of a compound of Formula I. In this embodiment, the compounds of the present invention can be used to control and treat infections due to various bacteria, but especially gram-positive bacteria. In a preferred embodiment, the compounds are used to control and treat infections due to bacteria resistant to existing antibacterials. For example, certain bacteria are resistant to methicillin, and yet others are resistant to vancomycin and/or teicoplanin. Strains of Enterococcus resistant to vancomycin are referred to as "VRE" (vancomycin-resistant Enterococcus); these strains represent a serious problem, especially in nosocomial settings. The present compounds provide a technique for controlling and treating infections due to VRE.

In carrying out this embodiment of the invention, the compounds can be administered by any of the conventional techniques, including the oral route and parenteral routes such as intravenous and intramuscular. The amount of compound to be employed is not critical and will vary depending on the particular compound employed, the route of administration, the severity of the infection, the interval between dosings, and other factors known to those skilled in the art. In general, a dose of from about 0.5 to about 100 mg./kg. will be effective; and in many situations, lesser doses of from about 0.5 to about 50 mg./kg. will be effective. A compound of the present invention can be administered in a single dose, but in the known manner of antibacterial therapy, a compound of the present invention is typically administered repeatedly over a period of time, such as a matter of days or weeks, to ensure control of the bacterial infection.

Also in accordance with known antibacterial therapy, a compound of the present invention is typically formulated for convenient delivery of the requisite dose. Therefore, in another embodiment, the present invention is directed to a pharmaceutical formulation comprising a compound of Formula I, in combination with a pharmaceutically-acceptable diluent or carrier. Such diluents and carriers are well known for both oral and parenteral routes of delivery. In general, a formulation will comprise a compound of the present invention in a concentration of from about 0.1 to about 90% by weight, and often from about 1.0 to about 3%.

The antibacterial efficacy of the present compounds is illustrated in TABLE 2. The minimal inhibitory concentrations (MICs) were determined using a standard broth microdilution assay.

TABLE 2

Enterococcus Screen, Minimum Inhibitory Concentrations (MICs)

| Ex. | Mean Values of 4–6 Isolates | | Selected Individual Pathogens* | | | | | | | |
|---|---|---|---|---|---|---|---|---|---|---|
| # | Resistant | Sensitive | SA 446 | SA 489 | SA 447 | SH105 | SH415 | SE270 | S PN P1 | S PY 203 |
| 1 | 1.4 | 0.13 | 4 | 2 | 1 | 2 | 2 | 0.25 | ≦0.125 | ≦0.06 |
| 2 | 1.19 | 0.041 | 1 | 1 | 0.5 | 0.125 | 0.25 | ≦0.06 | ≦0.06 | ≦0.06 |
| 3 | 2.4 | 0.11 | 2 | 4 | 2 | 0.5 | 2 | 1 | ≦0.06 | ≦0.06 |
| 4 | 2 | 0.082 | 2 | i | 0.5 | 1 | 2 | 0.125 | ≦0.06 | ≦0.06 |

TABLE 2-continued

Enterococcus Screen, Minimum Inhibitory Concentrations (MICs)

| Ex. # | Mean Values of 4–6 Isolates | | Selected Individual Pathogens* | | | | | | | |
|---|---|---|---|---|---|---|---|---|---|---|
| | Resistant | Sensitive | SA 446 | SA 489 | SA 447 | SH105 | SH415 | SE270 | S PN P1 | S PY 203 |
| 5 | 4 | 0.22 | 8 | 2 | 2 | 4 | 2 | 4 | | ≦0.06 |
| 6 | 1.7 | 0.44 | 4 | 2 | 1 | 1 | 4 | 1 | | ≦0.06 |
| 7 | 1.7 | 0.048 | 2 | 1 | 2 | 0.5 | 1 | 0.5 | ≦0.06 | ≦0.06 |
| 8 | 6.7 | 0.33 | 2 | 4 | 2 | 4 | 4 | 2 | ≦0.06 | ≦0.06 |
| 9 | 2 | 0.082 | 1 | 1 | 1 | 1 | 1 | 0.5 | ≦0.06 | ≦0.06 |
| 10 | 0.84 | 0.14 | 1 | 4 | 2 | 0.5 | 4 | 0.5 | ≦0.06 | ≦0.06 |
| 11 | 1 | 0.11 | 4 | 1 | 1 | 1 | 1 | 1 | ≦0.06 | ≦0.06 |
| 12 | 1.7 | 0.13 | 2 | 0.5 | 1 | 1 | 4 | 2 | ≦0.06 | ≦0.06 |
| 13 | 1.4 | 0.072 | 1 | 1 | 1 | 2 | 0.5 | 1 | ≦0.06 | ≦0.06 |
| 14 | 2 | 0.01 | 2 | 1 | 2 | 0.5 | 2 | 1 | ≦0.06 | ≦0.06 |
| 15 | 1.7 | 0.22 | 2 | 2 | 2 | 1 | 2 | 2 | ≦0.06 | ≦0.06 |
| 16 | 16 | 0.25 | 0.125 | ≦0.06 | ≦0.06 | ≦0.06 | 0.125 | ≦0.06 | ≦0.06 | |
| 17 | 1.4 | 0.25 | | | | | | | | |
| 18 | 0.84 | 0.19 | 1 | 2 | 1 | 2 | 2 | 1 | ≦0.06 | ≦0.06 |
| 19 | 1 | 0.22 | 2 | 2 | 4 | 2 | 4 | 2 | ≦0.06 | ≦0.06 |
| 20 | 11 | 0.22 | 0.125 | ≦0.06 | ≦0.06 | 0.125 | 0.25 | ≦0.06 | ≦0.06 | ≦0.06 |
| 21 | 1.2 | 0.054 | 4 | 2 | 2 | 0.5 | 2 | 0.5 | ≦0.06 | ≦0.06 |
| 22 | 1.68 | 0.87 | 32 | 32 | 32 | 8 | 8 | 16 | 0.125 | 0.125 |
| 23 | >128 | 0.44 | 0.125 | ≦0.06 | 0.125 | ≦0.06 | ≦0.06 | ≦0.06 | ≦0.06 | ≦0.06 |
| 24 | >128 | 0.38 | ≦0.06 | ≦0.06 | ≦0.06 | ≦0.06 | ≦0.06 | ≦0.06 | ≦0.06 | ≦0.06 |
| 25 | 2.8 | 5.0 | | | | | | | | |
| 26 | 1.7 | 0.44 | | 2 | 1 | 0.5 | 2 | 1 | 0.25 | 0.25 |

*SA 446 = *Staphylococcus aureus* 446
SA 489 = *Staphylococcus aureus* 489
SA 447 = *Staphylococcus aureus* 447
SH 105 = *Staphylococcus haemolyticus* 105
SH 415 = *Staphylococcus haemolyticus* 415
SE 270 = *Staphylococcus epidermis* 270
S PN P1 = *Streptococcus pneumoniae* P1
S PY 203 = *Streptococcus pyogenes* 203

We claim:
1. A compound of the formula:

[Structural formula I]

wherein $R^1$ is:
  —$CH_2R^2$;
wherein $R^2$ is:
  $R^3$,
  alkyl of $C_1$–$C_{11}$—$R^3$,
  alkenyl of $C_2$–$C_7$—$R^3$,
  alkynyl of $C_2$–$C_7$—$R^3$, or
  alkyl of $C_1$–$C_7$—O—$R^3$, wherein $R^3$ is a radical of the formula:

—$R_4$—[linker $_{(0\ or\ 1)}$—$R^4$]$_{(0\ or\ 1)}$ wherein each $R^4$ independently represents phenyl, cycloalkyl of $C_5$–$C_6$, naphthyl, or thienyl, each of which is unsubstituted or is optionally substituted with one or two substituents, each of which is independently alkyl of $C_1$–$C_{10}$, haloalkyl of $C_1$–$C_2$, haloalkoxy of $C_1$–$C_2$, alkoxy of $C_1$–$C_{10}$, halo, cyano, or nitro; and "linker" is:
  -alkylene of $C_1$–$C_3$,
  —O—alkylene of $C_1$–$C_6$,
  -alkylene of $C_1$–$C_6$—O—,
  —O—,
  —N(H or loweralkyl of $C_1$–$C_3$)—,
  —S—,
  —SO—,
  —SO$_2$—, $$-NH-\overset{O}{\underset{\|}{C}}-,\quad -\overset{O}{\underset{\|}{C}}-NH-,\quad -CH=CH-,$$

$$-C\equiv C-,\quad -N=N-,\quad -O-\overset{O}{\underset{\|}{C}}-, \text{ or }$$

$$-\overset{O}{\underset{\|}{C}}-O-;$$

and wherein $R^5$ is defined as follows:
  (1) each $R^5$ independently represents hydrogen, cycloalkyl of $C_5$–$C_6$,
cycloalkenyl of $C_5$–$C_6$,
phenyl or substituted phenyl bearing from one to three substituents, each of which is independently
  halo,
  nitro,
  loweralkyl of $C_1$–$C_4$,
  cycloalkyl of $C_5$–$C_6$,
  loweralkoxy of $C_1$–$C_4$,
  haloloweralkyl of $C_1$–$C_4$, or
  haloloweralkoxy of $C_1$–$C_4$;
naphthyl,
biphenylyl,
radical of the formula —$R^6$—$(R^7)_{0, 1, \text{ or } 2}$, wherein $R^6$ is loweralkyl of $C_1$–$C_8$ optionally substituted by from one to three substituents, each of which is independently selected from the group consisting of halo, nitro, cyano, loweralkoxy of $C_1$–$C_4$, haloloweralkyl of $C_1$–$C_4$, and haloloweralkoxy of $C_1$–$C_4$; and $R^7$ is

wherein each $R^8$ is independently hydrogen or loweralkyl of $C_1$–$C_4$ or one $R^8$ is hydrogen and the other $R^8$ is tert-butoxycarbonyl, or $R^7$ is phenyl or substituted phenyl as defined above, or (2) one $R^5$ is hydrogen and the other $R^5$ is (2-furanon-3-yl); or (3) both $R^5$s are taken together with the nitrogen and constitute a five- to seven-membered heterocyclic ring optionally containing in addition to the indicated nitrogen atom one additional hetero ring atom which is nitrogen, oxygen, or sulfur, and which heterocyclic radical can be unsubstituted or substituted with from one or two substituents, each of which is loweralkyl of $C_1$–$C_2$, loweralkoxy of $C_1$–$C_2$, phenyl, benzyl, or $C_1$–$C_6$-alkanoyl; or a salt thereof.

2. A compound of claim 1 wherein $R^1$ is 4-phenylbenzyl.

3. A compound of claim 2 which is $N^4$-(4-phenylbenzyl) A82846B, phenethylamide, or a salt thereof.

4. A compound of claim 2 which is $N^4$-(4-phenylbenzyl)-A82846B, benzylamide, or a salt thereof.

5. A compound of claim 2 which is $N^4$-(4-phenylbenzyl)-A82846B, methylamide, or a salt thereof.

6. A compound of claim 2 which is $N^4$-(4-phenylbenzyl)-A82846B, n-butylamide, or a salt thereof.

7. A compound of claim 2 which is $N^4$-(4-phenylbenzyl)-A82846B, (3-methoxypropyl)amide, or a salt thereof.

8. A compound of claim 2 which is $N^4$-(4-phenylbenzyl)-A82846B, 3-(dimethylamino)propylamide, or a salt thereof.

9. A compound of claim 1 wherein $R^1$ is 4-phenoxybenzyl.

10. A compound of claim 1 wherein $R^1$ is 4-(4-chlorophenyl)benzyl.

11. A pharmaceutical formulation comprising a compound of claim 1 in combination with a pharmaceutically-acceptable diluent or carrier.

12. A method of treating a bacterial infection in a host comprising the step of administering to the host an effective amount of a compound of claim 1.

13. A method of claim 12 wherein the bacterial infection is attributable to a vancomycin-resistant-enterococcus.

14. A process for the preparation of a compound of claim 1 which comprises reacting a compound of Formula II,

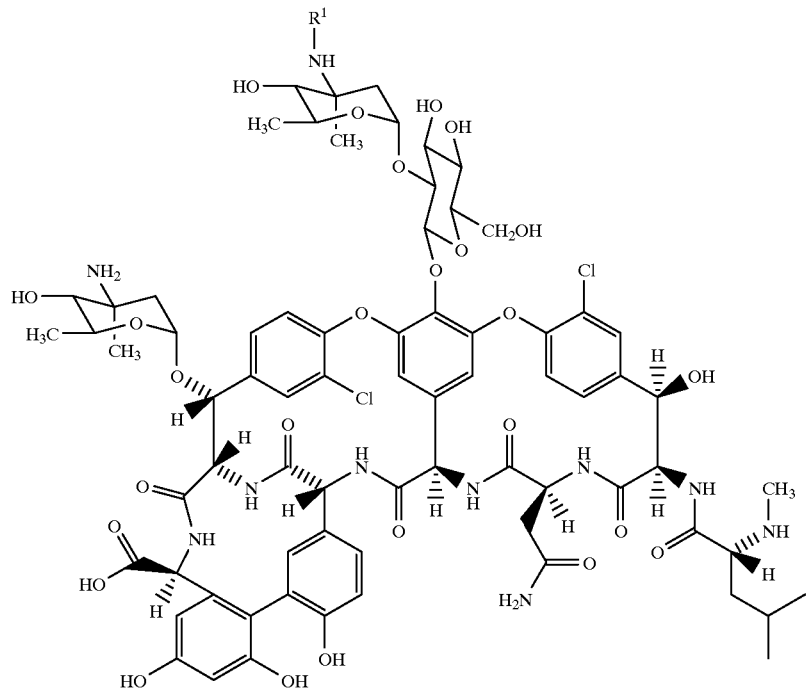

wherein $R^1$ is:
  hydrogen or —$CH_2R^2$;
wherein $R^2$ is:
  hydrogen,
  alkyl of $C_1$–$C_{15}$,
  alkenyl of $C_2$–$C_{15}$,
  alkynyl of $C_2$–$C_{15}$,
  haloalkyl of $C_1$–$C_7$,
  acenaphthenyl,
  2-fluorenyl,
  9,10-dihydro-2-phenanthrenyl,
  $R^3$,
  alkyl of $C_1$–$C_{11}$—$R^3$,
  alkenyl of $C_2$–$C_7$—$R^3$,
  alkynyl of $C_2$–$C_7$—$R^3$, or
  alkyl of $C_1$–$C_7$—O—$R^3$,
wherein $R^3$ is a radical of the formula:

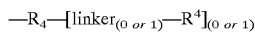

wherein each $R^4$ independently represents phenyl, cycloalkyl of $C_5$–$C_6$, naphthyl, or thienyl, each of which is unsubstituted or is optionally substituted with one or two substituents, each of which is independently alkyl of $C_1$–$C_{10}$, haloalkyl of $C_1$–$C_2$, haloalkoxy of $C_1$–$C_2$, alkoxy of $C_1$–$C_{10}$, halo, cyano, or nitro;
and "linker" is:
  -alkylene of $C_1$–$C_3$,
  —O—alkylene of $C_1$–$C_6$,
  -alkylene of $C_1$–$C_6$—O—,
  —O—,
  —N(H or loweralkyl of $C_1$–$C_3$)—,
  —S—,
  —SO—,
  —$SO_2$—,

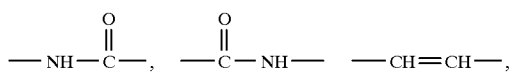

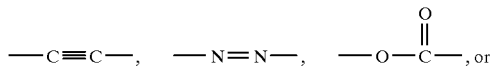

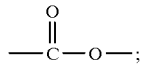

with an amine of the formula

wherein $R^5$ is defined as follows:
(1) each $R^5$ independently represents
  hydrogen,
  cycloalkyl of $C_5$–$C_6$.
  cycloalkenyl of $C_5$–$C_6$,
  phenyl or substituted phenyl bearing from one to three substituents, each of which is independently
    halo,
    nitro,
    loweralkyl of $C_1$–$C_4$,
    cycloalkyl of $C_5$–$C_6$,
    loweralkoxy of $C_1$–$C_4$,
    haloloweralkyl of $C_1$–$C_4$, or
    haloloweralkoxy of $C_1$–$C_4$;
  naphthyl,
  biphenylyl,
  radical of the formula —$R^6$—$(R^7)_{0, 1, or 2}$, wherein $R^6$ is loweralkyl of $C_1$–$C_8$ optionally substituted by from one to three substituents, each of which is independently selected from the group consisting of halo, nitro, cyano, loweralkoxy of $C_1$–$C_4$, haloloweralkyl of $C_1$–$C_4$, and haloloweralkoxy of $C_1$–$C_4$; and $R^7$ is

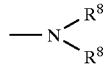

wherein each $R^8$ is independently hydrogen or loweralkyl of $C_1$–$C_4$ or one $R^8$ is hydrogen and the other $R^8$ is tert-butoxycarbonyl, or $R^7$ is phenyl or substituted phenyl as defined above, or
(2) one $R^5$ is hydrogen and the other $R^5$ is (2-furanon-3-yl); or
(3) both $R^5$s are taken together with the nitrogen and constitute a five- to seven-membered heterocyclic ring optionally containing in addition to the indicated nitrogen atom one additional hetero ring atom which is nitrogen, oxygen, or sulfur, and which heterocyclic radical can be unsubstituted or substituted with from one or two substituents, each of which is loweralkyl of $C_1$–$C_2$, loweralkoxy of $C_1$–$C_2$, phenyl, benzyl, or $C_1$–$C_6$-alkanoyl; and optionally forming a salt thereof.

* * * * *